United States Patent [19]

Accorsi et al.

[11] Patent Number: 5,549,870
[45] Date of Patent: Aug. 27, 1996

[54] SELF-SUPPORTING THIN-FILM FILAMENT DETECTOR, PROCESS FOR ITS MANUFACTURE AND ITS APPLICATION TO GAS DETECTION AND GAS CHROMATOGRAPHY

[75] Inventors: Antoinette Accorsi, Pont Sainte Maxence; Daniel Charlot, Saint Ismier, both of France

[73] Assignees: Commissariat a l'Energie Atomique; Institute National de l'Environnement Industriel et des Risques, both of France

[21] Appl. No.: 345,548

[22] Filed: Nov. 28, 1994

Related U.S. Application Data

[63] Continuation of Ser. No. 829,074, filed as PCT/FR90/00608 Aug. 10, 1990 published as WO91/02242 Feb. 21, 1991, abandoned.

[30] Foreign Application Priority Data

Aug. 11, 1989 [FR] France ................................ 89 10837

[51] Int. Cl.⁶ .................................................. G01N 27/12
[52] U.S. Cl. .................................................. 422/90; 422/94
[58] Field of Search .................................. 422/90, 94–98; 73/23.31, 25.03, 25.05, 335.05; 338/22, 50, 24, 34; 324/451, 71.5

[56] References Cited

U.S. PATENT DOCUMENTS

| | | | |
|---|---|---|---|
| 4,902,138 | 2/1990 | Goeldner et al. | 73/25.03 X |
| 4,938,928 | 7/1990 | Koda et al. | 422/95 X |
| 4,991,424 | 2/1991 | Lehto | 73/25.05 X |

FOREIGN PATENT DOCUMENTS

| | | |
|---|---|---|
| 0313390 | 10/1988 | European Pat. Off. . |
| 0377792 | 7/1990 | European Pat. Off. . |
| 3028249 | 2/1981 | Germany . |
| 3743398 | 7/1989 | Germany . |
| 2158586 | 11/1985 | United Kingdom . |

*Primary Examiner*—Jeffrey Snay
*Attorney, Agent, or Firm*—Remy J. VanOphem; John VanOphem; Thomas A. Meehan

[57] ABSTRACT

Detector of the filament type for determining a static or dynamic characteristic of an ambient medium, constituted by a resistive component intended to be heated by the Joule effect in the medium, and an interface region suitable for reacting with the medium by a physico-chemical process with an effect, depending on the characteristic to be determined, on the electrical characteristic of the interface region, in which there is a supporting member through which there is at least one aperture and at least one filament including the resistive component, composed of one or more thin films and a central portion located in the aperture and end portions via which the central portion is connected to the supporting member.

14 Claims, 7 Drawing Sheets

5,549,870

SELF-SUPPORTING THIN-FILM FILAMENT DETECTOR, PROCESS FOR ITS MANUFACTURE AND ITS APPLICATION TO GAS DETECTION AND GAS CHROMATOGRAPHY

This is a continuation of application Ser. No. 07/829,074, filed as PCT/FR90/00608, Aug. 10, 1990 published as WO91/02242, Feb. 21, 1992, now abandoned.

BACKGROUND OF THE INVENTION

The present invention concerns a filament type sensor for determining a static or dynamic characteristic of a gas environment such as the air, for example, a method of fabricating it, and applications of the sensor primarily to the detection of oxidizable gases but also to gas chromatography (detection of ionizable gases) and fluid flowrate measurement.

A filament type sensor of this kind has a resistive element within a filament adapted to exchange heat with the environment and an interface area adapted to react with the environment in a physico-chemical process. In the broadest possible sense of the term, this process includes catalysis of combustion, adsorption, ionization, simple thermal exchange, as well as others which influence an electrical characteristic of the interface area, i.e., temperature or resistance, voltage, current, etc., according to the characteristic of the environment to be determined, for example, concentration, flowrate, etc. The interface area can be the external portion of the resistive element, or a catalyst film heated by conduction, or a separate electrode.

Some sensors of this kind are based on measuring the heat exchanged (detection of combustible gases, flowmeter, etc) and may be characterized as calorimetric sensors. There are also various filament type sensors having the common feature of measuring a concentration, based on various phenomena; for example, measurement of the heat exchanged in the case of detecting combustible or oxidizable gases, or measurement of the quantities of ions captured by an electrode in gas chromatography. Filament type sensors are, therefore, of very diverse kinds, both with regard to the physico-chemical phenomenon on which their operation is based and with regard to the nature of the parameter to be measured.

Although the remainder of this description refers for the most part to the detection of an oxidizable gas in a gas environment such as the air, in the field of explosimetry, for example, this is a preferred application and is not limited to the invention.

A known way of detecting an oxidizable gas in the air uses a filament, usually of platinum, heated by the Joule effect, i.e. by the passage of an electric current. The oxidizable gas contained in the surrounding air is oxidized by catalysis in contact with the filament, so that the latter is further heated. The resulting temperature variation causes a variation in the resistance of the filament, which is measured directly or indirectly to obtain the concentration of the oxidizable gas in the air. These filament-based detectors are largely handmade. They, therefore, suffer from a lack of reproducibility and high cost. Their low electrical resistance and their low surface area/volume ratio make it necessary to operate them at high temperatures, for example, about 1000° C.

Other oxidizable gas detectors are based on catalytic beads; they are formed by a metal detector, of platinum, for example, coated with alumina doped with a catalyst, and resemble a small pearl. These detectors age less rapidly, as the associated combustion temperature is lower. However, these beads have the disadvantage of significant drift in sensitivity, reduced stability and an increased response time as compared with filaments.

A third type of oxidizable gas detector is based on semiconductor metal oxides doped with a catalyst. These detectors are formed by a metal heating element which heats an insulative material (alumina, for example) sleeve onto which is deposited a film of semiconductor material whose resistance variations are measured. These detectors are sensitive to any gas that can be absorbed onto the surface of the semiconductor. They have a relatively long response time, however, and the further disadvantage of high electrical power consumption; also, the effects of humidity are not compensated.

The invention is directed to alleviating the aforementioned disadvantages by improving reproducibility and by reducing thermal losses from the filament by conduction, while also reducing manufacturing costs.

SUMMARY OF THE INVENTION

In a very general way, the invention proposes a filament type sensor for determining a static or dynamic characteristic of a surrounding environment, having a resistive element adapted to be heated in the environment by the Joule effect and an interface area adapted to react with the environment in a physico-chemical process influencing an electrical characteristic of the interface area according to the characteristic to be determined. The sensor has a supporting wafer through which there is formed at least one aperture and at least one filament including the resistive element, composed of one or more thin films and having a central portion situated in the aperture and at least two end portions by which the central portion is connected to the supporting wafer.

In other words, the invention proposes a filament fabricated using microelectronics technology in such a way that it is "self-supporting", meaning that the only connections between it and the support are thin films. The filament is, therefore, composed of one or more "floating" thin films, which considerably reduces thermal losses by conduction.

The invention results from the observation that thin film technology can be used to produce a filament having sufficient mechanical strength and thermal shock resistance for it to be self-supporting.

It has been found that, despite the thinness of the filament which confers upon it the necessary electrical resistance, it is both sufficiently sensitive with respect to the physico-chemical reaction on which the measurement is based and sufficiently strong that it is not worn out prematurely through contact with the surrounding environment.

According to preferred features of the invention, the filament is formed by a film of a metal catalyst whose exterior surface constitutes the interface area. At least the central portion of the filament is formed by at least three superimposed thin films constituting a conductive material film extending to the ends of the filament, a catalyst film forming the interface area and an electrically insulative material intermediate film. The resistive element of the filament is a film of a noble metal such as platinum, gold or palladium or a combination of noble metals. The filament has a sinuous shape, for example, a crenellated shape, and the central portion of the filament is connected to the substrate by more than two end portions. The substrate is chosen from the group of materials including glass, silicon, alumina, silica, quartz and polymers and the interface area is a thin film deposited on at least one surface of the substrate near the aperture.

The invention also proposes a filament preparation method using microelectronics technology suitable for fabricating the aforementioned sensor utilizing the following steps:

depositing onto the front and rear surfaces of a wafer-form substrate a thin film front mask incorporating a front window, the shape of which reflects the shape of the filament to be fabricated and has a central portion extended by end portions, and a thin film rear mask incorporating a rear window facing the central portion of the window excluding the ends, but larger than the central portion;

hollowing a trench into the substrate by etching the front surface of the substrate through the front mask;

depositing onto the back of the trench one or more thin films adapted to constitute the filament, at least one of the thin films being an electrically conductive material; and eliminating the substrate to its full thickness by etching it through the rear mask.

According to the preferred features of the invention, before the substrate is etched through the rear mask to eliminate its entire thickness, a protective film is deposited onto the front surface and into the trench and the protective film is eliminated after the substrate is etched; the protective film on the front surface is a polymer resin; and the front mask is an intermediate film covered with a film of resin, the thin films of the filament being deposited, after elimination of the resin film, by deposition of one or more thin films into and around the trench followed by elimination of the thin films deposited outside the trench by etching the intermediate film.

The main advantages of the invention as compared with all the previously mentioned detector elements are very low electrical power consumption and a very short response time.

The sensor can be manufactured automatically and in multiples and can, therefore, be fabricated in large quantities at low cost.

The sensor's resistance depends on its geometrical shape and allows an operating temperature lower than conventional filament type sensors, which results in good measurement resolution and slower aging. It is relatively insensitive to impact due to its novel construction and its resulting very low mass.

Because its thermal inertia is very low, it can be used for measurements at different temperatures and in very short time intervals.

The invention also resides in applications of a sensor of this kind, principally to detecting oxidizable gases such as methane or carbon monoxide and also to gas chromatography (detection of ionizable gases) and to the calorimetric measurement of gas flowrates.

Other objects, features, and advantages of the invention will emerge from a reading of the following description taken in conjunction with the accompanying drawings.

DETAILED DESCRIPTION OF THE PREFERRED EMBODIMENT

Figure 1:
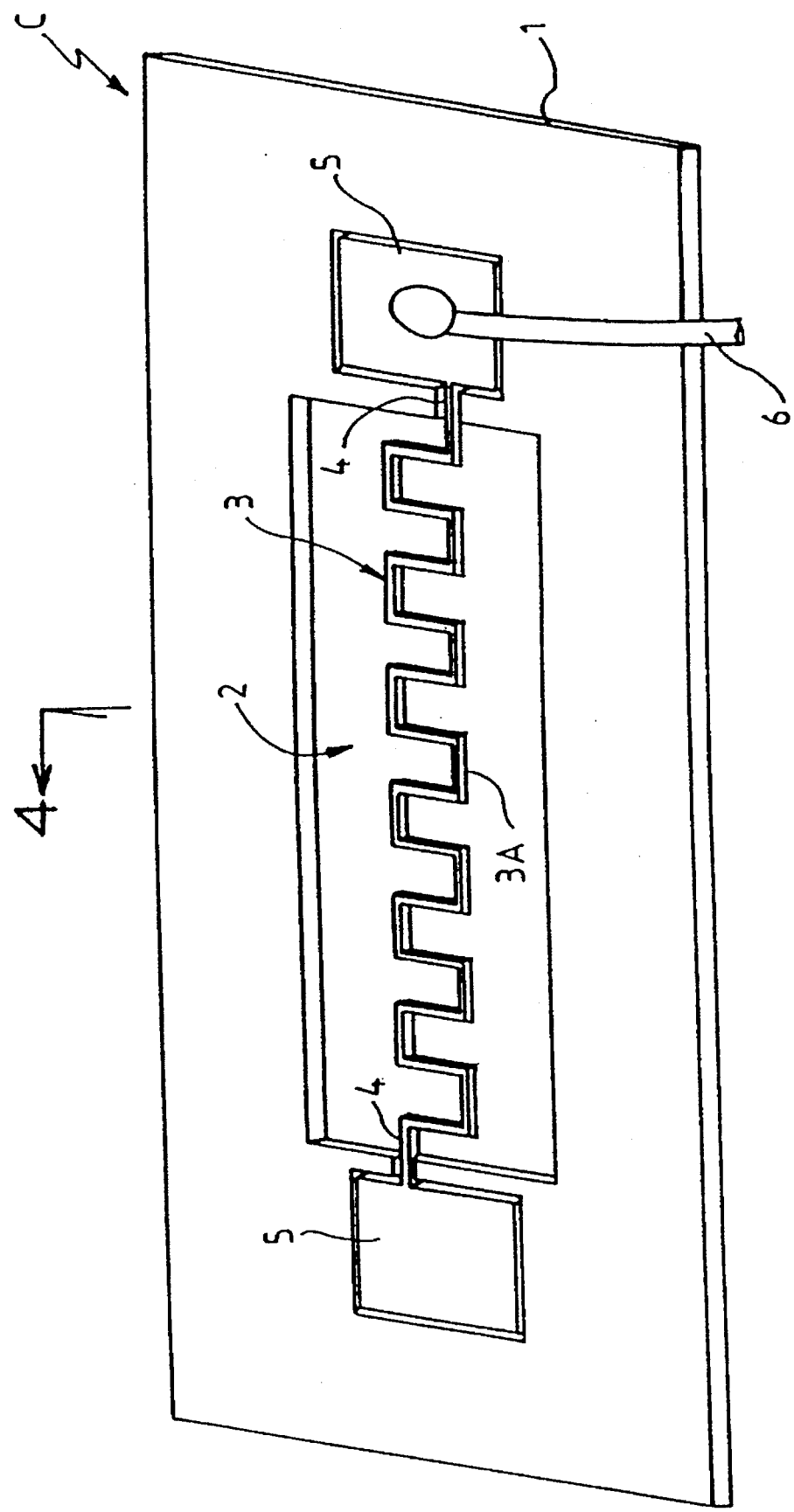
FIG. 1 is a perspective view of a sensor in accordance with the invention.

A sensor C depicted in FIG. 1 constitutes a support wafer 1 made from glass or some other insulative (or semiconductor) material with an aperture 2 through it. As an alternative, the support wafer may be made from an insulative or non-insulative material covered with an insulative film.

Across the aperture is a filament 3 in the form of a thin film of an electrically conductive material whose outer surface or skin constitutes an interface area with the surrounding environment.

The filament 3 has a central portion 3A and electrically conductive ends 4 by which the central portion 3A is connected to the support wafer 1. The ends 4 terminate at conductive lands 5 to which electrical wires 6 connecting the sensor to the remainder of the electric circuit including it can be connected, by soldering, for example.

The filament 3 preferably has a sinuous shape parallel to the support wafer 1, in this instance a crenellated shape. For a given cross-section and a given distance between the lands 5 this increases its surface area and reduces the risk of rupture due to thermal expansion. Other geometrical shapes are possible, of course. The thin film filament 3 need not be rectilinear overall, but could be curved parallel to the support wafer 1. The filament 3 could equally well be in the form of a thin plate parallel to the support wafer 1, with dimensions less than those of the aperture 2.

The thin film filament 3 may be produced from any substance giving rise to the physico-chemical phenomena on which the measurements are based; in this instance the thin film filament 3 is made from a material chosen to have electrical properties which are modified by the environment to be characterized.

In the particular instance of oxidizable gas measurement, it may be a catalyst: platinum, nickel, osmium, gold, irridium, combinations of metals, metal oxides, semiconductors, sulfides, etc.

The material may also be chosen according to its absorbent or adsorbent properties if they modify its electrical characteristics.

Figure 2:
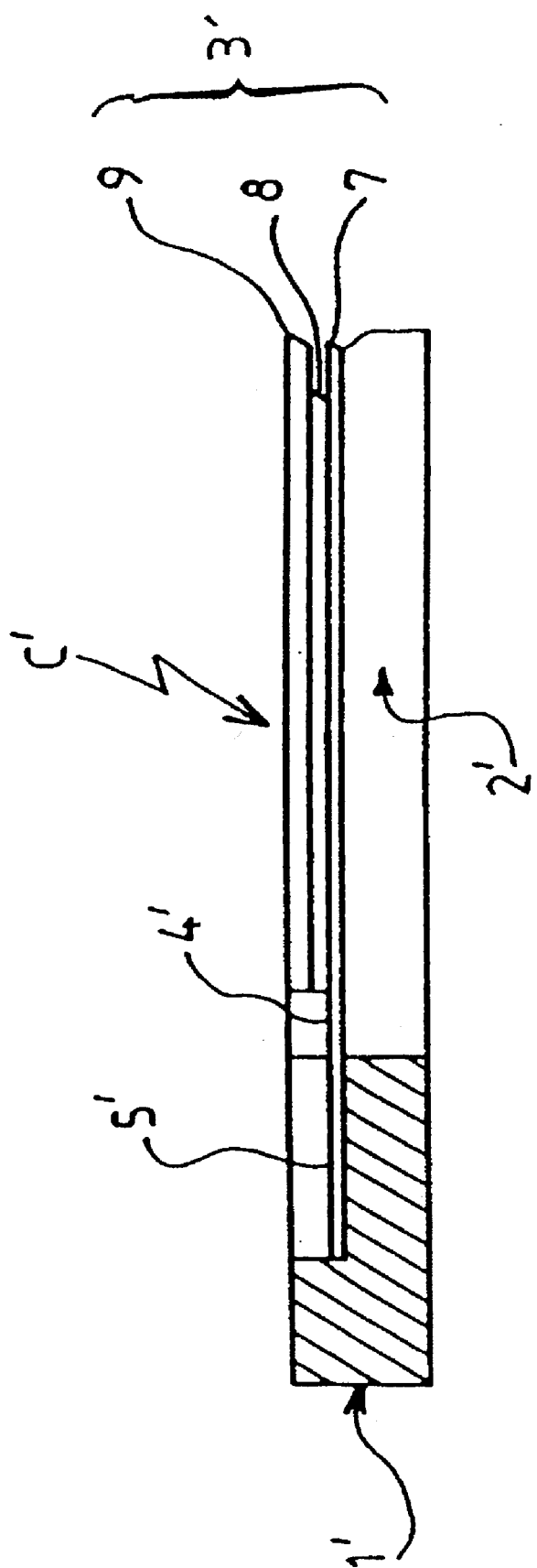
FIG. 2 is a partial view of another sensor in longitudinal cross-section in the direction of its thickness.

In FIG. 2 parts similar to parts of FIG. 1 have the same reference number with a "prime" suffix. This figure shows another sensor C' whose filament 3' is not a single thin film but a stack of thin films of conductive or insulative material or catalyst. The succession of these films is such that each catalyst film is at the top or bottom of the stack; each electrically conductive film is electrically connected to the lands 5; and insulative film is provided between the conductive material or catalyst films.

To be more precise, FIG. 2 shows three successive films 7, 8 and 9, respectively of conductive material, insulative material, and catalyst. In an alternative embodiment that is not shown the films are stacked with a 9-8-7-8-9 arrangement.

Figure 3:
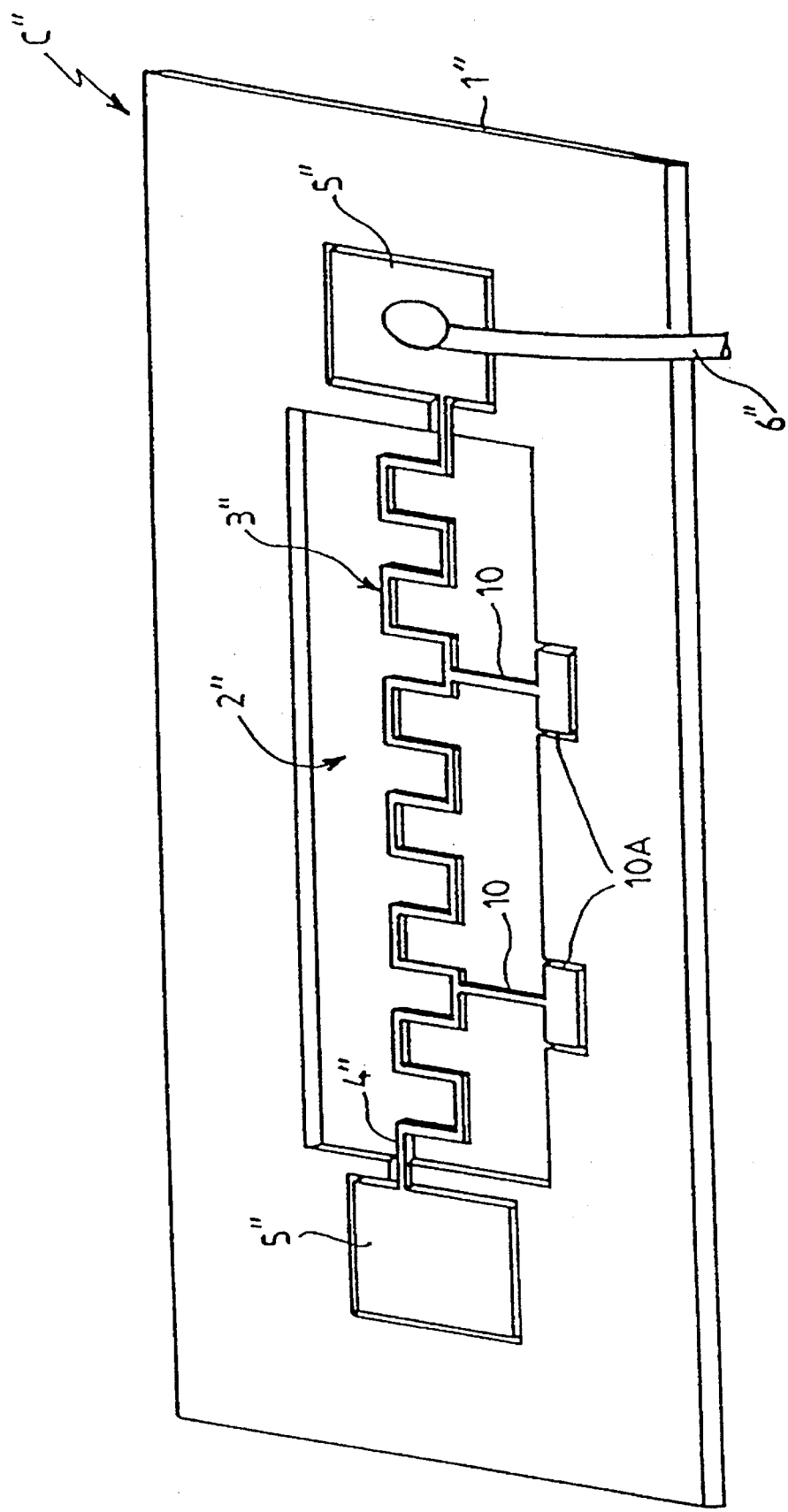
FIG. 3 is an alternate embodiment of the sensor depicted in FIG. 1.

In FIG. 3 parts similar to parts of FIG. 1 have the same reference number with a "double prime" suffix. The figure shows another variant C" of FIG. 1 in which additional end portions 10 are disposed transversely to the central portion of the filament 3". These additional portions end at lands 10A. In the case of a single-film filament as in FIG. 1, they can be used for intermediate electrical measurements or in different circuits, so reducing the number of different sensors to be manufactured and stored for a given number of applications. In the case of a multiple film filament as in FIG. 2, the end portions 10 may be electrical connections to the catalyst film which is otherwise insulated from the conductive film.

It will be understood that in each of the foregoing examples all of the filament is entirely contained within the overall thickness of the substrate.

FIGS. 4 through 9 show in cross-section, as viewed in a direction along line 4—4 in FIG. 1, various stages in the manufacture of the sensor, a glass substrate being used in this example.

A first phase entails preparing the substrate by cleaning it using nitric or sulfochromic acid, for example, followed by rinsing with deionized water, and drying under dust-free conditions.

In a second phase masks are prepared on each of front and rear surfaces 1A and 1B of the substrate, in stages, as follows (see FIG. 4).

Figure 5:
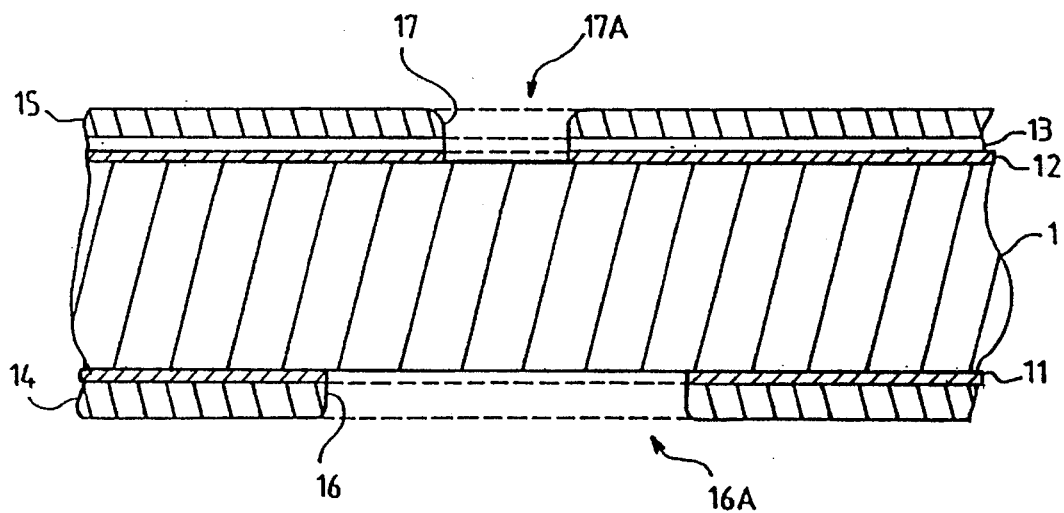

A thin film 11 of chromium with a thickness of 1000 to 2000 Å is deposited onto the rear surface; a film 12 of chromium between a few Å and 1000 Å thick and then a film 13 of gold approximately 1000 Å thick are deposited onto the other (front) surface; these stages may be staggered with respect to each other but are preferably simultaneous; a film 14 and 15 of photosensitive resin is deposited onto the front and rear surfaces 1A and 1B, respectively, of the substrate; exposure masks 14A and 15A are positioned on opposite sides of the substrate and face their corresponding films 14 and 15, respectively, such that the films 14 and 15 are exposed through the masks 14A and 15A and the exposed areas are developed which produces resin masks 16 and 17; the metal films are etched through the masks 16 and 17, i.e., etching of the chromium film 11 on the rear surface, etching of the gold film 13 on the front surface, and etching of the chromium film 12 on the front surface; and further rinsing with deionized water, resulting in the structure shown in FIG. 5.

It will be understood that the rear mask obtained in this way (films 11 and 14) includes a window 16A facing the central portion (between the ends 4 and 5 in FIG. 1) of the window 17A in the front mask (films 12, 13 and 15), to the exclusion of the ends, but the window 16A is larger (in this instance wider on each side) than the central portion.

In a third phase hydrofluoric acid is used to etch trenches 18 and 19 into the glass through the masks consisting of the superimposed films of chromium 12, gold 13 and resin 15 etched onto the front surface 1A of the support wafer 1. This etching is isotropic in the direction of the thickness and laterally; the resulting undercutting leaves the films 12 and 13 projecting over inclined edges 20 of the trench to form an overhang 21. Although it is standard practice with etching methods of this type to modify the process conditions to avoid such undercutting, in this instance such undercutting is deliberate and useful. The resulting overhang 21 allows improved removal of the films 12 and 13 at the end of fabrication.

The resin masks 14 and 15 are removed, for example, using acetone and then nitric acid. The resulting structure is then rinsed with deionized water and dried under dust-free conditions, yielding the structure depicted in FIG. 6.

Figure 7:
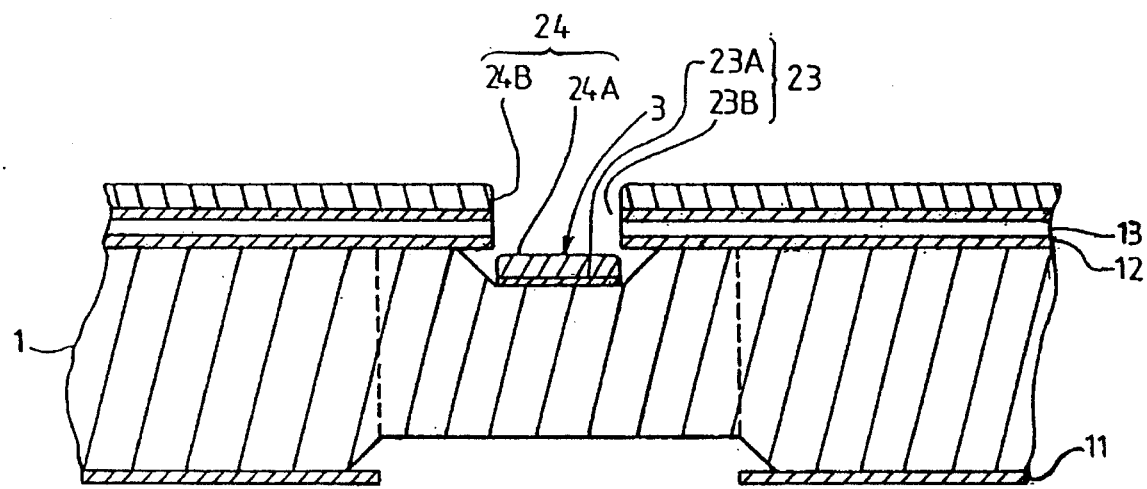

In a fourth stage the filament 3 is formed at the bottom of the trench 18 by depositing a thin film 23 of chromium (approximately 100 Å thick) onto the front surface 1A of the substrate, including onto the bottom of the trench 18, followed by the deposition of a film 24 of platinum over all of the thin film 23 (see FIG. 7). There are obtained in this way thin films 23A and 24A of chromium and platinum in the trench dissociated from portions 23B and 24B of chromium and platinum deposited on the remainder of the front surface 1A. The overall thickness of the films 23 and 24 must, therefore, be at least slightly less than the depth of the trench 18. In the case of the sensor C' from FIG. 2 the equivalent condition is that the overall thickness of the deposited films must be less than the depth of the trench. It is essential that the films in the trench 18 do not come into contact with the overhangs 21.

The side portions of the excess platinum and chromium films 24A and 23A are then eliminated by chemical etching of the gold film 13 (immersion of the substrate for at least three hours in a gold etching reagent which mechanically eliminates the superfluous film of platinum, with the final traces of excess platinum removed in an ultrasonic cleaning tank). This operation is greatly facilitated by the overhang 21 obtained by undercutting.

Figure 4:
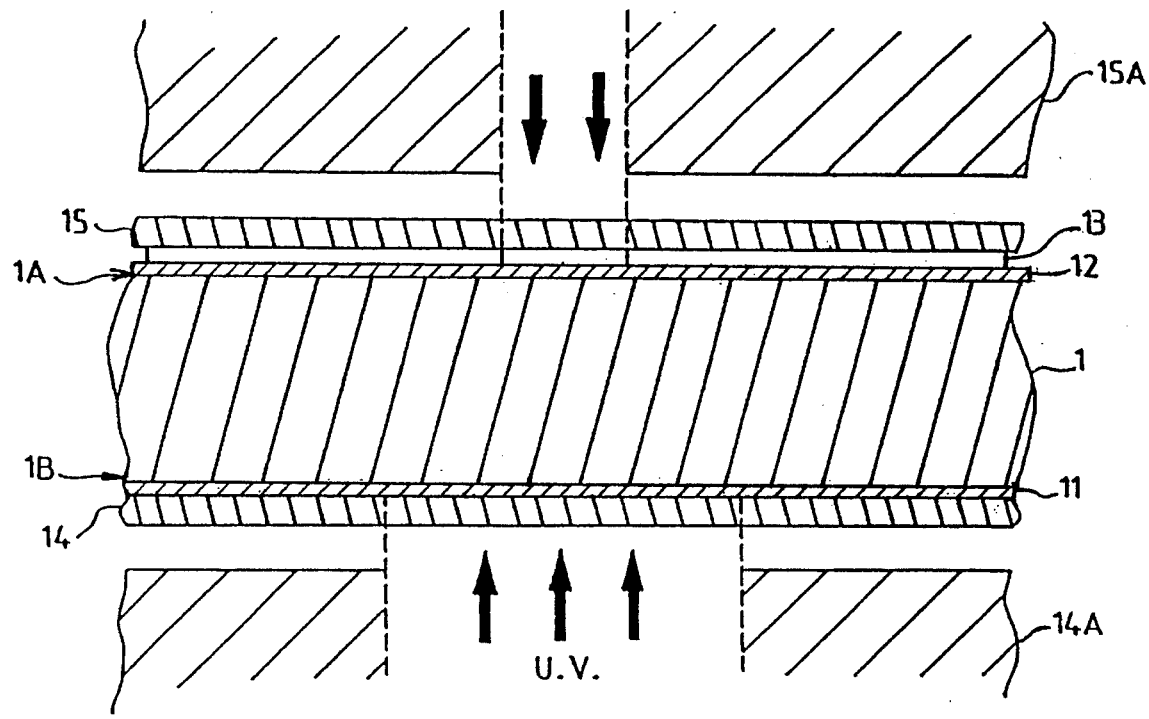
FIGS. 4, 5a, 5b, 6a, 6b and 7 through 9 are views of the sensor in a direction along line 4—4 of FIG. 1 in cross-section at various stages in its fabrication on a substrate by the method in accordance with the invention.

Following rinsing with deionized water and drying a new film 25 of photosensitive resin approximately 3 Im thick is deposited onto the rear surface and is then exposed through the same mask as in FIG. 4. Following development, a rear mask is obtained coincident with the chromium mask 11 remaining on this surface; in practice the mask is then cured at 140° C. for 30 minutes.

In a final phase the substrate is hollowed out through its entire thickness by an etching process through the rear mask, in the following stages.

A protective film 26 is deposited on the front surface 1A covered with the chromium film 12; this protective film 26 fills the trench 18 and by adhering to it covers the filament 3 at its bottom; this protective film 26 may be of any material which is resistant to hydrofluoric acid and can be easily dissolved using a commercially available solvent; a ZIVI APIEZON-W type polymer resin is preferably used; and the support wafer or glass 1 carrying the filament 3 is chemically etched with ultrasonic agitation through the mask 25 deposited onto the rear surface 1B and consisting of the chromium film 11 and the etched photosensitive resin film 25.

Figure 9:
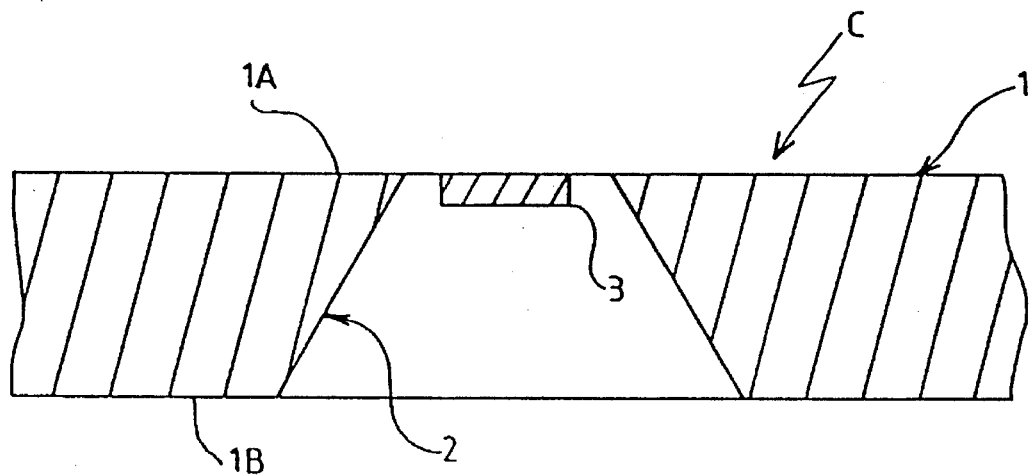

After the glass and the protective film 26 are removed using an appropriate commercially available solvent, such as perchlorethylene, for example, the filament 3 is, surprisingly, found to be "self-supported" in the glass support wafer 1 (see FIG. 9). All traces of resin and polymer are removed from the glass support wafer 1 using an appropriate chemical reagent (usually fuming nitric acid) and the remaining chromium films 11 and 12 on each side of the glass support wafer 1 are removed using the reagent for chemical etching of chromium.

Figure 8:
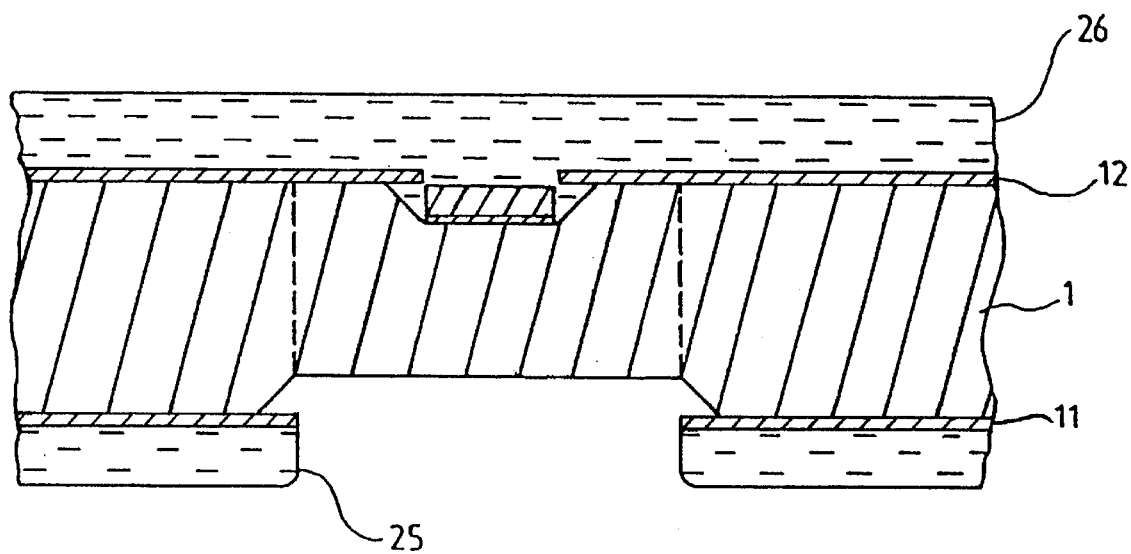

The inclined flanks of the aperture 2 in FIG. 9 result from the isotropic nature of the etching by hydrofluoric acid. In the case of a substrate and an acid producing anisotropic etching, vertical flanks would be obtained as shown in FIGS. 7 and 8.

Specific examples of the chemical etching reagents used are:

chromium:
   1) SOPRELEC (EVRY) Cr-ETCH
   2) 50 g/l of KMn04+50 g/l of KOH+1 l of deionized water, gold: 25 g/l of I2=60 g/l of KI+1 l of deionized water,
glass: HF diluted 40% to 20% (according to the required etching rate).

Examples of thicknesses for glass wafers 150 Im thick are:
chromium No 11: 500 to 1000 Å,
chromium Nos 12 and 23: 50 to 500 Å,
gold No 13: 1500 to 2500 Å,
platinum: 0.5 to 9 Im,
W apiezon: 100 Im minimum,
SHIPPLEY 1350-H photosensitive resin: 1 to 3 Im,
length of hole: 2 mm.

The benefits of the chromium films 11 and 12 are firstly the improved deposition of the gold film 13, which could not be achieved directly onto the glass, and secondly the high strength of the mask formed by the photosensitive resin 14 and 15 and chromium films 11 and 12 during etching of the glass with hydrofluoric acid.

Figure 5B:
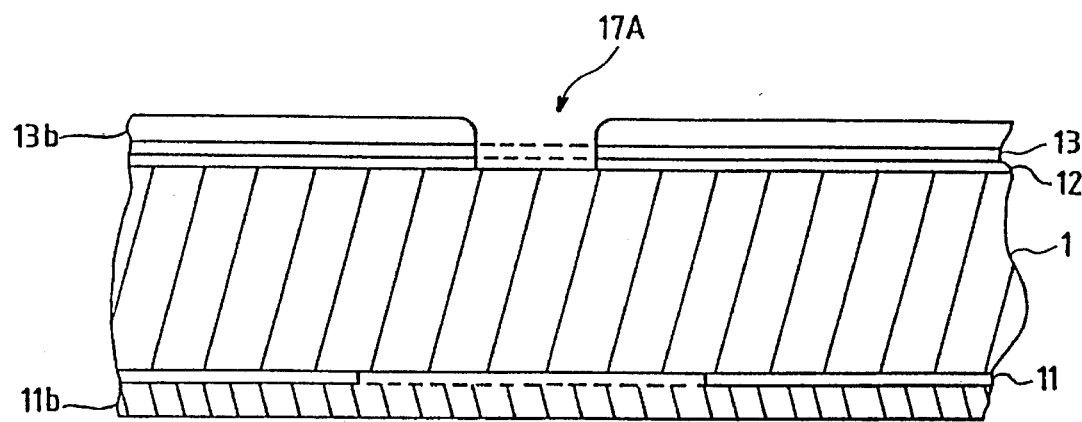
Figure 6B:
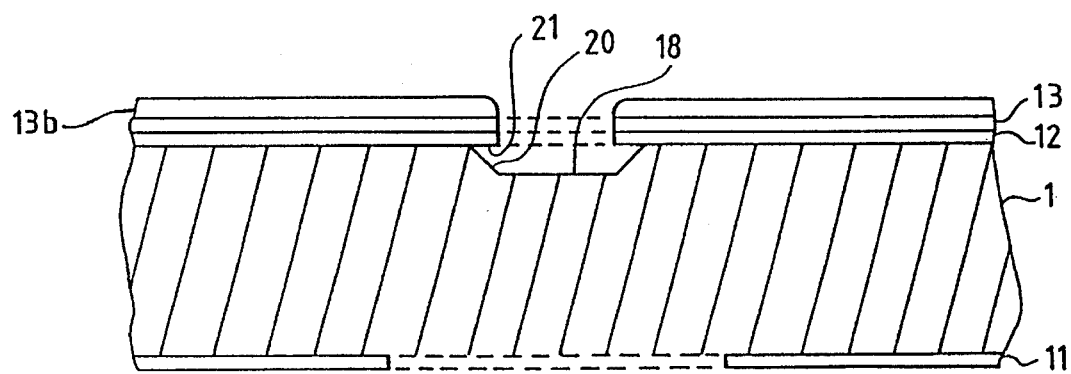
Figure 6A:
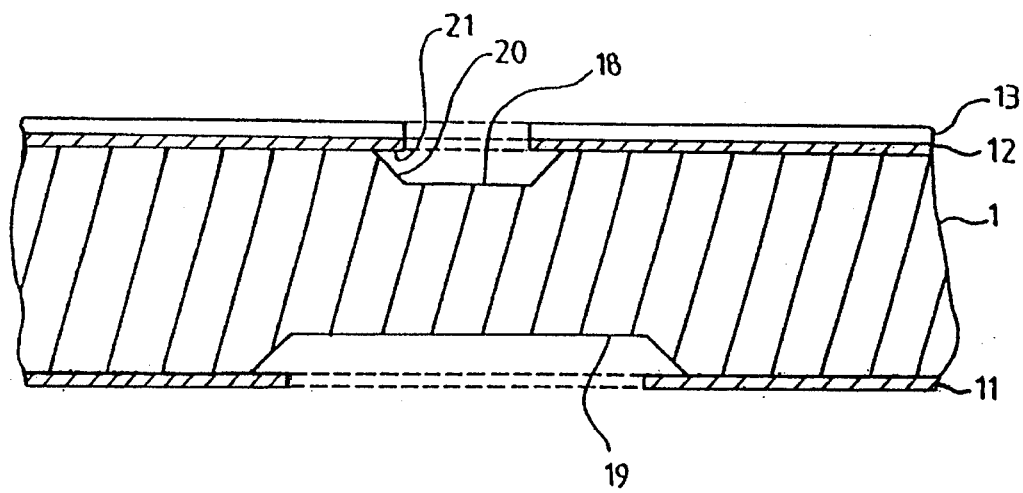

In a variant of the method shown in FIGS. 5b and 6b the gold film 13 and 13b is thickened. This makes it possible to deposit a greater thickness of platinum (as represented by film 24 in FIG. 7).

The second and third phases of the method are modified as follows.

After etching the metal through the masks 16 and 17, the resin layers 14 and 15 are cleaned using acetone and nitric acid, and further rinsing is then carried out using deionized water.

It will be realized that the resulting rear mask (layer 11) constitutes a window 16A facing the central portion (between the ends 4 in FIG. 1) of the window 17A in the front mask (layers 12, 13) excluding the ends but that this window 16A is wider (in this instance wider on each side) than the central portion.

The gold film 13 is then thickened (FIG. 5b) by electrolytically depositing gold (film 13b) followed by rinsing with deionized water.

The thickness of the electrolytic gold plating (film 13b) is determined by the depth of the trenches to be etched in the next stage and is approximately 1 Im for a trench depth of 10 to 15 Im. A uniform film 11b of protective photosensitive resin is deposited onto the rear surface.

In the third phase hydrofluoric acid is used to etch the trench 18 into the glass through the mask consisting of the superimposed films 12 of chromium and 13 and 13b of gold etched onto the front surface 1A of the support wafer 1. This etching is isotropic in the direction of the thickness and laterally; the resulting undercutting leaves the films 12, 13 and 13b projecting over the inclined edges 20 of the trench to form an overhang 21. Although it is standard practice with etching methods of this type to modify the process conditions to avoid the undercutting, in this instance such undercutting is deliberate and useful. The resulting overhang 21 allows improved removal of the films 12 and 13 at the end of fabrication.

The resin mask 11b is removed, for example using acetone and then nitric acid. The resulting structure is then rinsed with deionized water and dried under dust-free conditions, yielding the structure of FIG. 6.

Subsequent stages of the process are exactly the same as before.

In addition to glass it is possible to use other substrates, for example, silicon, alumina, silica and especially quartz which offers good heat resistance and selective resistance to etching.

It is also possible to use double-sided metal-plated substrates, for example, gold over chromium, which means that the first metal deposition stages can be omitted.

Trials have been conducted on quartz between 125 and 175 Im thick plated with gold over chromium on both sides using the same chemical etchant reagents.

There are diverse applications for a sensor of this kind.

First, it can be used to detect oxidizable gas by integrating a described known circuit.

Second, it can also be used for chromatographic measurements. The filament 3 is used to heat and locally ionize the gaseous medium and one or more ion receiving electrodes (interface area) are constituted by one or more conductive thin films deposited onto the substrate near the aperture 2. The chromium films 11 and 12 may be left in place for this purpose.

It goes without saying that the present invention has been described by way of non-limiting example only and that numerous variants can be put forward by one skilled in the art without departing from the scope of the invention. For example, multiple filaments may be formed in a single hole and multiple holes may be formed in a single substrate.

What is claimed is:

1. A sensor for determining a static or dynamic characteristic of a surrounding environment, comprising:
   a supporting substrate through which there is formed at least one aperture and having at least two conductive lands at a side area of said at least one aperture;
   at least one elongated filament comprising at least one elongated thin film of an electrically conductive element, said at least one elongated filament having a central portion and at least two end portions, said central portion being only attached to said at least two conductive lands of said supporting substrate by said at least two end portions, said central portion between said at least two end portions independently spanning said at least one aperture, said central portion further being connected through said at least two end portions and said at least two conductive lands to said supporting substrate; and
   an interface region integral with said at least one elongated filament, said interface region being adapted to react with the environment so as to modify a predetermined electrical characteristic of said interface region, whereby static or dynamic characteristics of a surrounding environment may be measured.

2. A sensor according to claim 1 wherein said at least one elongated filament is formed by a film of a metal catalyst whose exterior surface constitutes said interface region.

3. A sensor according to claim 1 wherein said at least one elongated filament is formed by at least three superimposed thin films, said at least three superimposed thin films comprising said at least one elongated thin film of an electrically conductive element extending to said at least two end portions, a catalyst material forming said interface region and an electrically insulative material intermediate said at least one thin elongated film of an electrically conductive element and said catalyst material.

4. A sensor according to claim 1 wherein said at least one thin elongated film of an electrically conductive element is a film of a noble metal chosen from the group consisting of platinum, gold palladium and a combination of said noble metals.

5. A sensor according to claim 1 wherein said at least one elongated filament has a sinuous shape.

6. A sensor according to claim 1 wherein said central portion of said at least one elongated filament is connected to said supporting substrate by more than said at least two end portions.

7. A sensor according to claim 1 wherein said supporting substrate is chosen from the group consisting of glass, silicon, alumina, silica, quartz and polymers.

8. A sensor according to claim 1 wherein said interface region further comprises means for varying said predetermined electrical characteristic with the flowrate of at least one fluid.

9. A sensor according to claim 1 wherein said interface region further comprises means for reacting with at least one oxidizable gas.

10. A sensor according to claim 9 wherein said at least one oxidizable gas is methane or carbon monoxide.

11. A sensor according to claim 1 wherein said interface region is a thin film deposited on at least one surface of said supporting substrate proximate to said at least one aperture.

12. A sensor according to claim 11 wherein said interface region further comprises means for reacting with at least one ionizable gas.

13. A sensor for determining a static or dynamic characteristic of a surrounding environment, comprising:

a supporting substrate through which there is formed at least one aperture and having at least two conductive lands positioned at a side area of said at least one aperture;

at least one elongated filament comprising at least one elongated thin film of an electrically conductive element, said at least one elongated filament having a central portion and at least two end portions, said central portion being only attached to said at least two conductive lands of said supporting substrate by said at least two end portions, said central portion between said at least two end portions independently spanning said at least one aperture, said central portion further being electrically connected through said at least two end portions and said at least two conductive lands to said supporting substrate; and a catalyst interface region integral with said at least one elongated filament, said catalyst interface region reacting by catalytic oxidation with oxidizable gases.

14. A sensor for determining a static or dynamic characteristic of a surrounding environment, comprising:

a supporting substrate through which there is formed at least one aperture and having at least two conductive lands at a side area of said at least one aperture;

at least one elongated filament having a substantially constant cross section throughout the entire length of said at least one elongated filament, said at least one elongated filament comprising at least one elongated thin film of an electrically conductive element, said at least one elongated filament having a central portion and at least two end portions, said central portion being only attached to said at least two conductive lands of said supporting substrate by said at least two end portions, said central portion between said at least two end portions independently spanning said at least one aperture, said central portion further being electrically connected through said at least two end portions and said at least two conductive lands to said supporting substrate; and an interface region integral with said at least one elongated filament, said interface region being adapted to react with the environment so as to modify a predetermined electrical characteristic of said interface region, whereby static or dynamic characteristics of a surrounding environment may be measured.

* * * * *

UNITED STATES PATENT AND TRADEMARK OFFICE
CERTIFICATE OF CORRECTION

PATENT NO. : 5,549,870
DATED : August 27, 1996
INVENTOR(S) : Accorsi et al

It is certified that error appears in the above-indentified patent and that said Letters Patent is hereby corrected as shown below:

Column 8, line 57, after "gold" insert ---- , ----.

Signed and Sealed this

First Day of July, 1997

Attest:

BRUCE LEHMAN

*Attesting Officer*  *Commissioner of Patents and Trademarks*